US006197935B1

(12) United States Patent
Doillon et al.

(10) Patent No.: US 6,197,935 B1
(45) Date of Patent: Mar. 6, 2001

(54) PRION-FREE COLLAGEN AND COLLAGEN-DERIVED PRODUCTS AND IMPLANTS FOR MULTIPLE BIOMEDICAL APPLICATIONS; METHODS OF MAKING THEREOF

(75) Inventors: Charles Doillon, Montchatel; Régen Drouin, Sainte-Foy; Gaétan LaRoche, Saint-Augustin, all of (CA)

(73) Assignee: DiagnoCure, Inc., Sainte-Foy (CA)

( * ) Notice: Subject to any disclaimer, the term of this patent is extended or adjusted under 35 U.S.C. 154(b) by 0 days.

(21) Appl. No.: 09/117,378

(22) PCT Filed: Jan. 29, 1997

(86) PCT No.: PCT/CA97/00070

§ 371 Date: Sep. 29, 1998

§ 102(e) Date: Sep. 29, 1998

(87) PCT Pub. No.: WO97/28192

PCT Pub. Date: Aug. 7, 1997

Related U.S. Application Data

(60) Provisional application No. 60/010,794, filed on Jan. 29, 1996.

(51) Int. Cl.[7] ............................ A61K 38/17; C07K 14/78; A61L 15/00
(52) U.S. Cl. ............................ 530/356; 530/412; 530/427; 514/2; 514/21; 514/801; 424/422; 424/444; 424/445
(58) Field of Search ............................ 530/356, 412, 530/421, 427; 514/2, 21, 801; 424/422, 444, 445

(56) References Cited

U.S. PATENT DOCUMENTS

| 4,060,081 | 11/1977 | Yannas et al. ........................ 128/156 |
| 4,511,653 | * 4/1985 | Play et al. ............................ 435/69.1 |
| 4,642,117 | * 2/1987 | Nguyen et al. ........................ 623/11 |

OTHER PUBLICATIONS

Safar et al., *Prot. Sci.*, vol. 2, pp. 2206–2216, Dec. 1993.*
Doillon et al., *J. Biomed. Res.*, vol. 37, pp. 212–221, 1997.*
Berg, R.A., "Determination of 3–and 4–Hydroxyproline," *Meth. Enzymol.* 82 Pt.A:372–398 (1982).
Brown, P., et al., "Resistance of Scrapie infectivity to Steam Autoclaving after Formaldehyde Fixation and Limited Survival after Ashing at 360°C: Practical and Theoretical Implications," *J. Infect. Dis.* 161:467–472 (Mar. 1990).
CôtéM.–F., , "In vitro contraction rate of collegan in sponge–shape matrices," *J. Biomater. Sci., Polymer Edn.* 3:301–313 (Apr. 1992).
DeBlois, C., et al., "Heparin–fibroblast growth factor–fibrin complex: in vitro and in vivo applications to collagen–based materials," *Biomater.* 15:665–672 (Jul. 1994).

Drouin, R., et al., "Agarose Gel Electrophoresis for DNA Damage Analysis," in: *Technologies for Detection of DNA Damage and Mutations*, Pfeifer, G.P., ed., Plenum Press, New York, Chapter 3, pp. 37–43 (1996).
Ellender, G., et al., "Osteogenic Capacity of Collagen in Repair of Established Periodontal Defects," *Clin. Mater.* 9:201–209 (Apr. 1992).
Ellwart, J.W., and Dörmer, P., "Vitality Measurement Using Spectrum Shift in Hoechst 33342 Stained Cells," *Cytometry* 11:239–243 (Mar. 1990).
Griffiths, P.R., and Pariente, G.L., "Introduction to spectral deconvolution," *Trends Anal. Chem.* 5:209–215 (Sep. 1986).
Kajava, A.V., "Molecular Packing in Type I Collagen Fibrils. A Model with Neighbouring Collagen Molecules Aligned in Axial Register," *J. Mol. Biol.* 218:815–823 (Apr. 1991).
Keefe, J., et al., "Clinical Use of injectable Bovine Collagen: A Decade of Experience," *Clin. Mater.* 9:155–162 (Apr. 1992).
Klunk, W.E., et al., "NMR Identification of the Formic Acid–Modified Residue in Alzheimer's Amyloid Protein," *J. Neurochem.* 62:349–354 (Jan. 1994).
Koide, M., et al., "A new type of biomaterial for artificial skin: Dehydrothermally cross–linked composites of fibrillar and denatured collagens," *J. Biomed. Mat. Res.* 27:79–87 (Jan. 1993).
Lazarev, Y.A., et al., "Amide I Band of IR Spectrum and Structure of Collagen and Related Polypeptides," *Biopolymers* 24:1449–1478 (Aug. 1985).

(List continued on next page.)

*Primary Examiner*—Christopher S. F. Low
*Assistant Examiner*—Abdel A. Mohamed
(74) *Attorney, Agent, or Firm*—Sterne, Kessler, Goldstein & Fox P.L.L.C.

(57) ABSTRACT

The use of collagen as a biomedical implant raises safety issues towards viruses and prions. The physicochemical changes and the in vitro and in vivo biocompatibility of collagen treated with heat, and by formic acid (FA), trifluoroacetic acid (TFA), tetrafluoroethanol (TFE) and hexafluoroiso-propanol (HFIP) were investigated. FA and TFA resulted in extensive depurination of nucleic acids while HFIP and TFE did so to a lesser degree. The molecules of FA, and most importantly of TFA, remained within collagen. Although these two acids induced modification in the secondary structure of collagen, resistance to collagenase was not affected and, in vitro, cell growth was not impaired. Severe dehydrothermal treatment, for example 110° C. for 1–3 days under high vacuum, also succeeded in removing completely nucleic acids. Since this treatment also leads to slight cross-linking, it could be advantageously used to eliminate prion and to stabilize gelatin products. Finally, prolonged treatment with TFA provides a transparent collagen, which transparency is further enhanced by adding glycosaminoglycans or proteoglycans, particularly hyaluronic acid. All the above treatments could offer a safe and biocompatible collagen-derived material for diverse biomedical uses, by providing a virus or prion-free product.

15 Claims, 9 Drawing Sheets

OTHER PUBLICATIONS

Lee, J.M., et al., "A multi–sample denaturation temperature tester for collagenous biomaterials," *Med. Eng. Phys.* 17:115–121 (Mar. 1995).

Miller, E.J., and Rhodes, R. K., "Preparation and Characterization of the Different Types of Collagen," *Meth. Enzymol. 82 Pt.A*:33–64 (1982).

Miyata, T., et al., "Collagen Engineering for Biomaterial Use, " *Clin. Mater.9*:139–148 (Apr. 1992).

Payne, K.J., and Veis, A., "Fourier Tranform IR Spectroscopy of Collagen and Gelatin Solutions: Deconvolution of th Amide I Band for Conformational Studies," *Biopolymers* 27:1749–1760 (Nov. 1988).

Prusiner, S.B., "Novel Proteinaceous Infectious Particles Cause Scrapie," *Science 216*:136–144 (Apr. 1982).

Prusiner, S.B., "Inherited prion diseases," *Proc. Natl. Acad. Sci. USA 91*:4611–4614 (May 1994).

Rosenberg, R.N., et al., "Precautions in Handling Tissues, Fluids, and Other Contaminated Materials from Patients with Documented or Suspected Creutzfeldt–Jakob Disease," *Ann. Neurol. 19*:75–77 (Jan. 1986).

Safar, J., et al., "Thermal stability and conformational transitions of scrapi amyloid (prion) protein correlate with infectivity," *Prot. Sci. 2*:2206–2216 (Dec. 1993).

Tateishi, J., et al., "Inactivation of the Creutzfeldt–Jacob Disease Agent," *Ann. Neurol. 24*:466 (Sep. 1988).

Yoshizato, K., and Yoshikawa, E., "Development of bilayered gelatin substrate for bioskin: a new structural framework of the skin composed of porous dermal matrix and thin basement membrane," *Mater. Sci. Eng. C1*:95–105 (1994).

\* cited by examiner

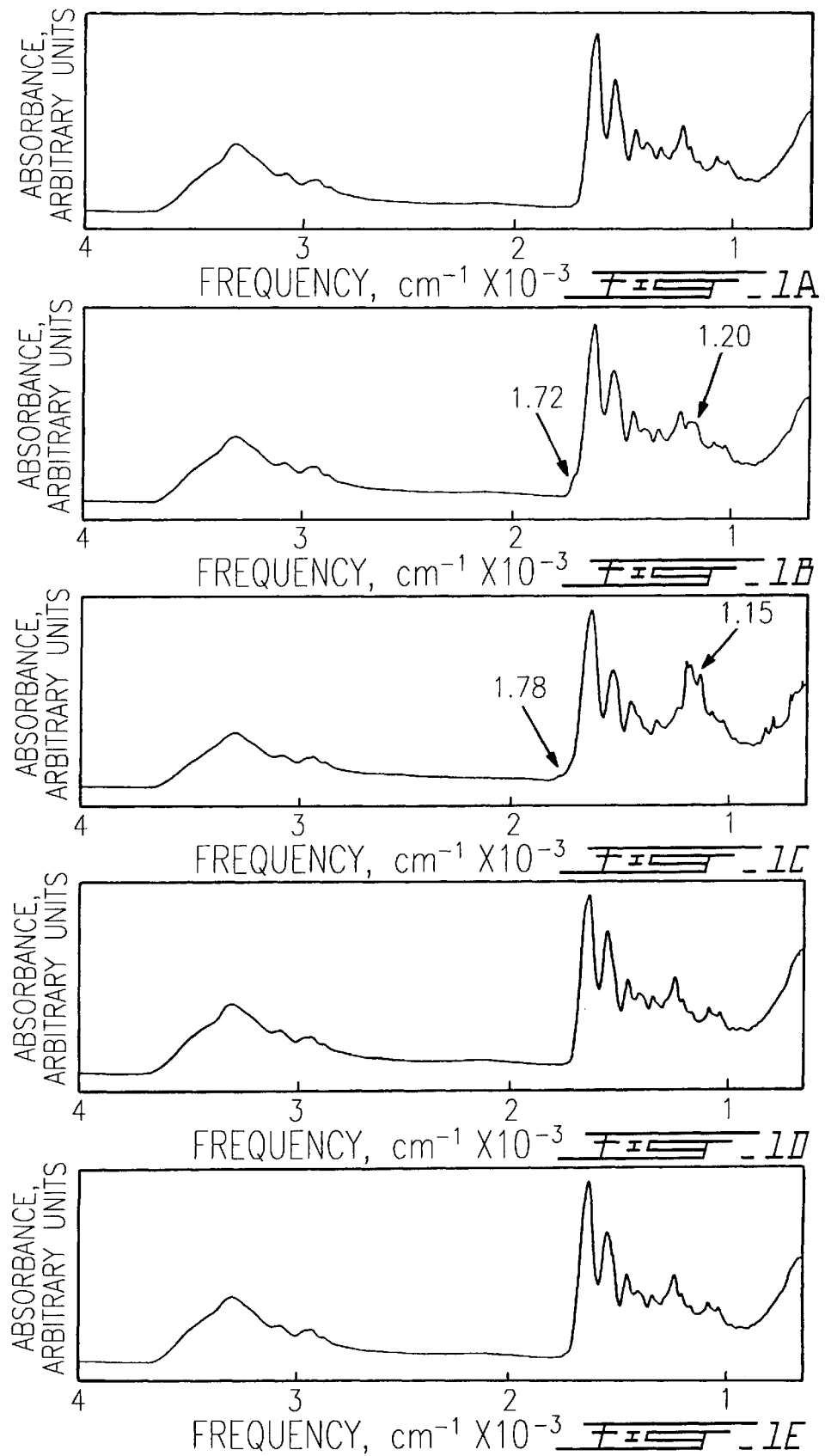

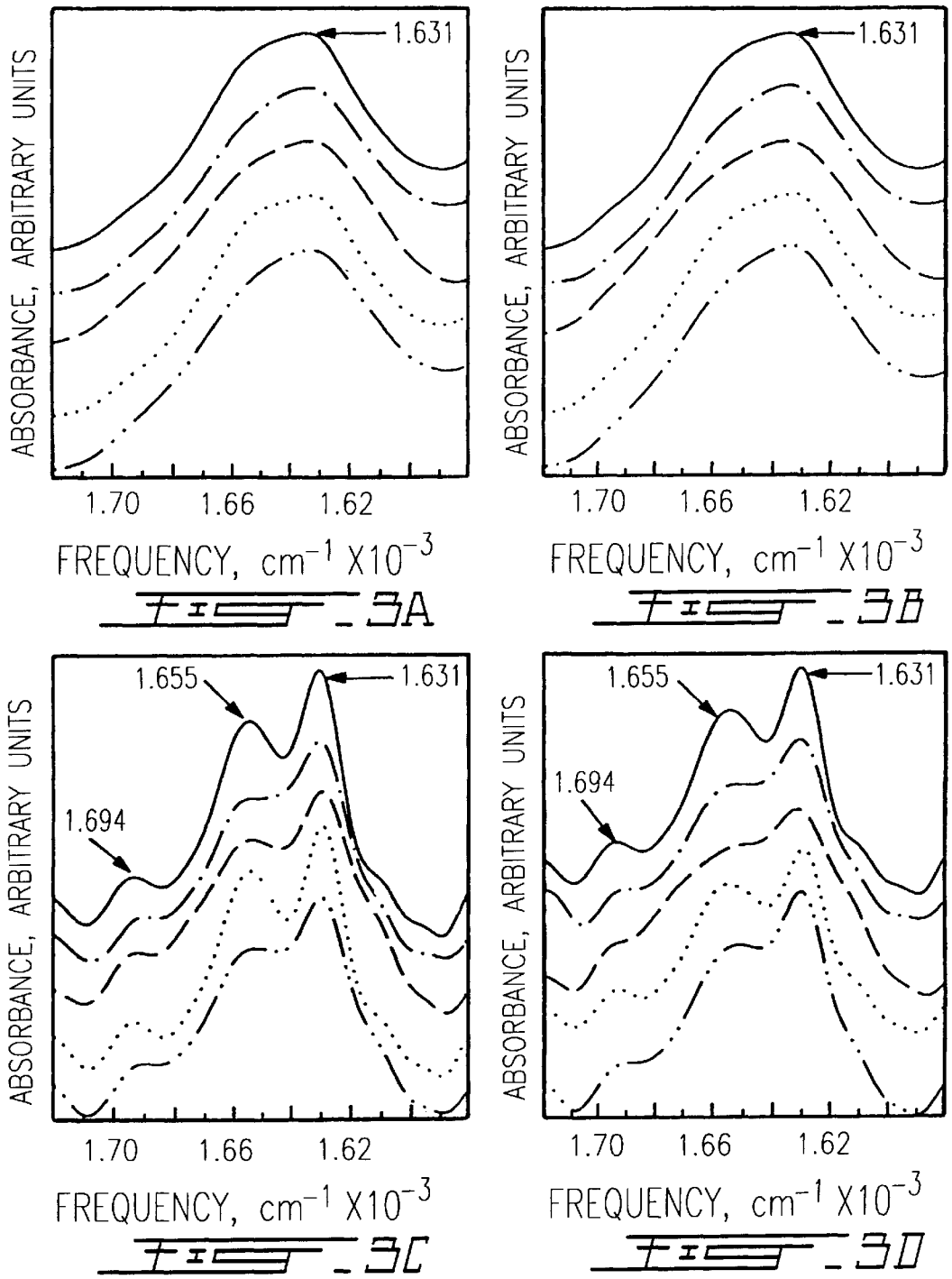

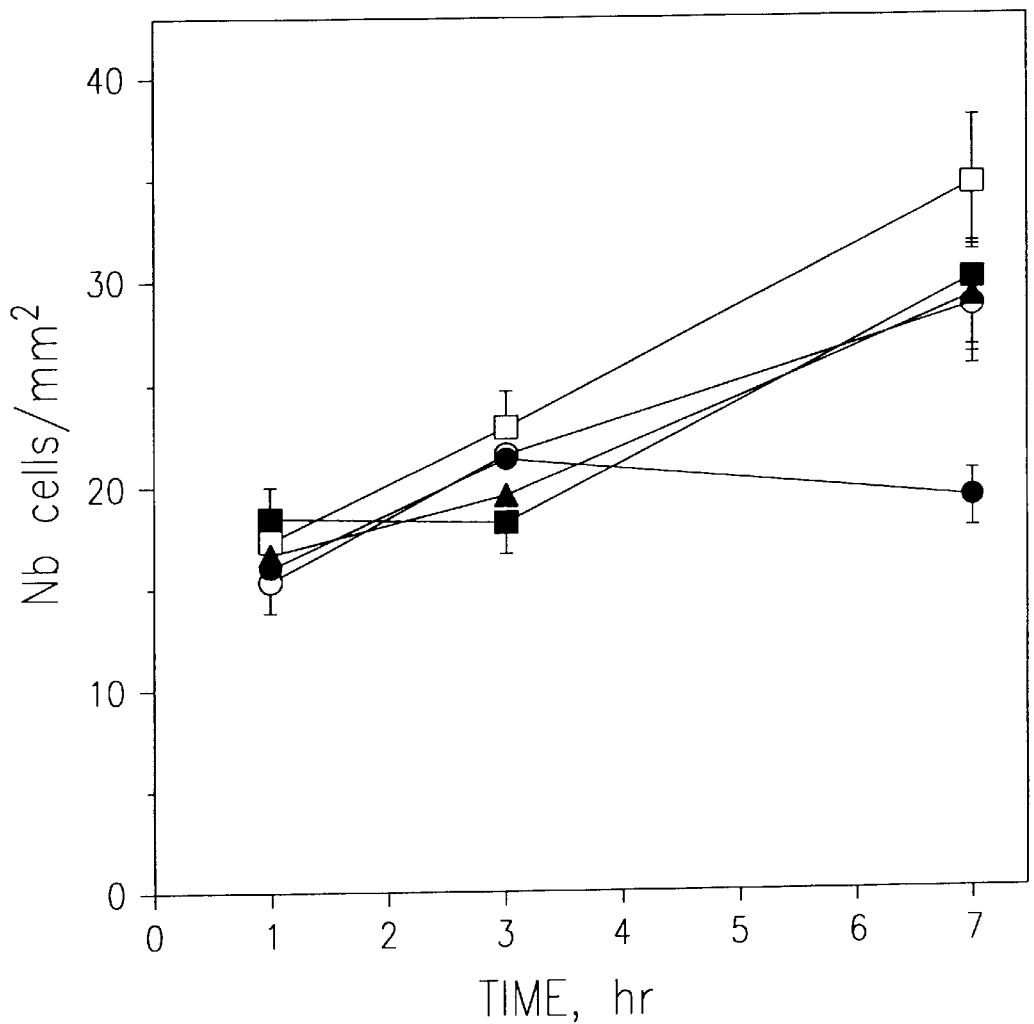
FIG_4

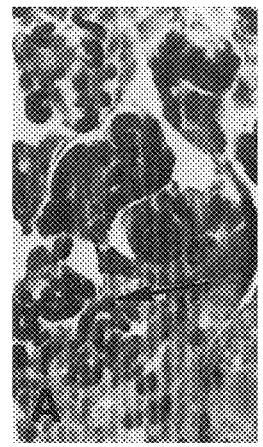
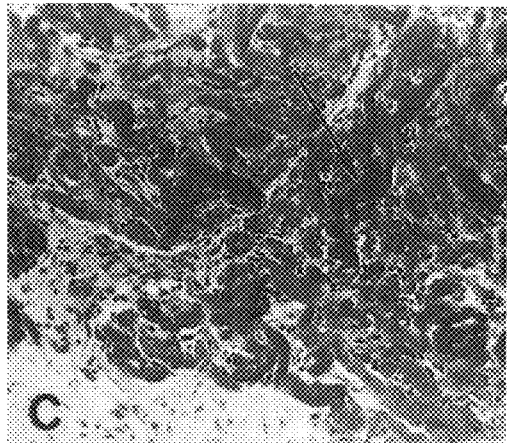
FIG. 5A  FIG. 5B  FIG. 5C
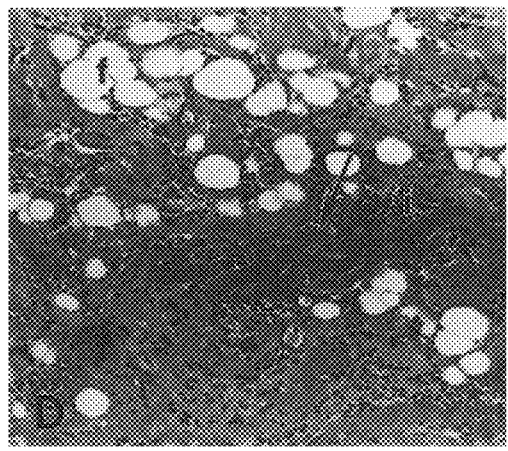
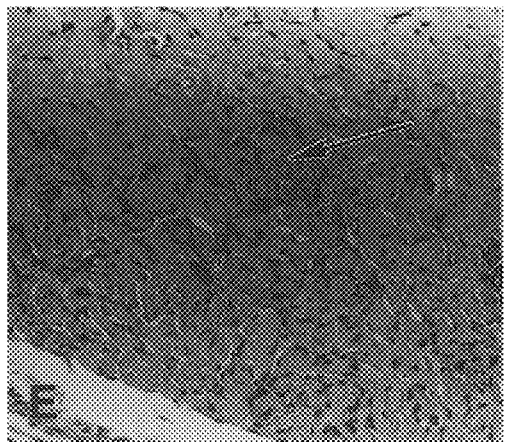
FIG. 5D  FIG. 5E

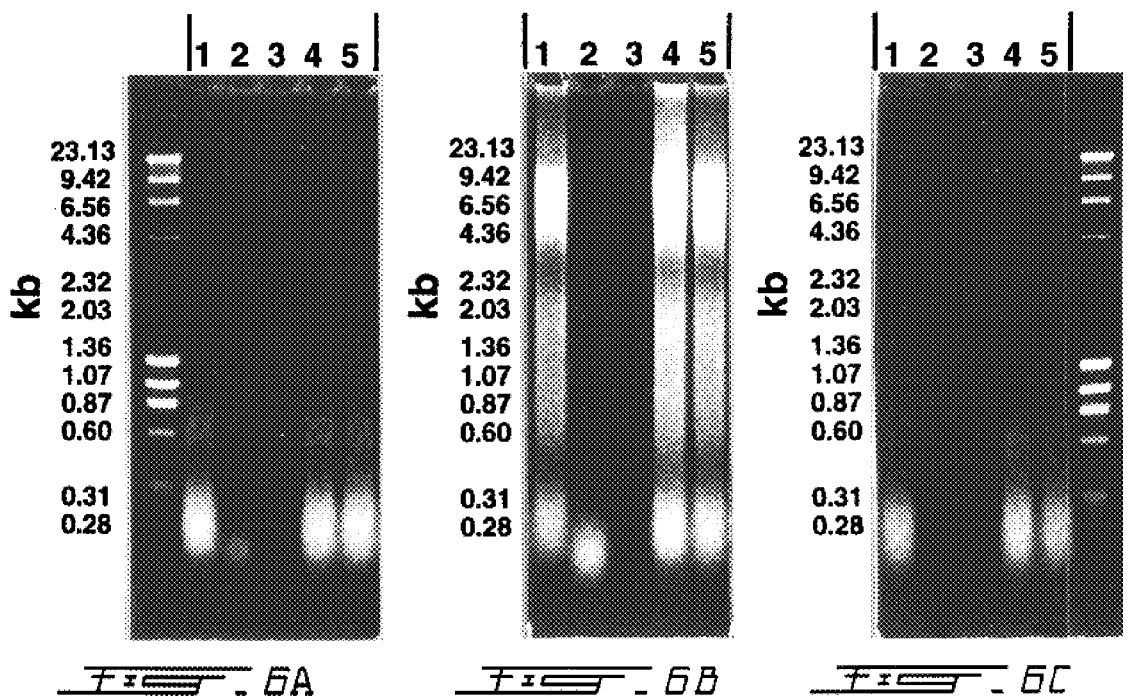

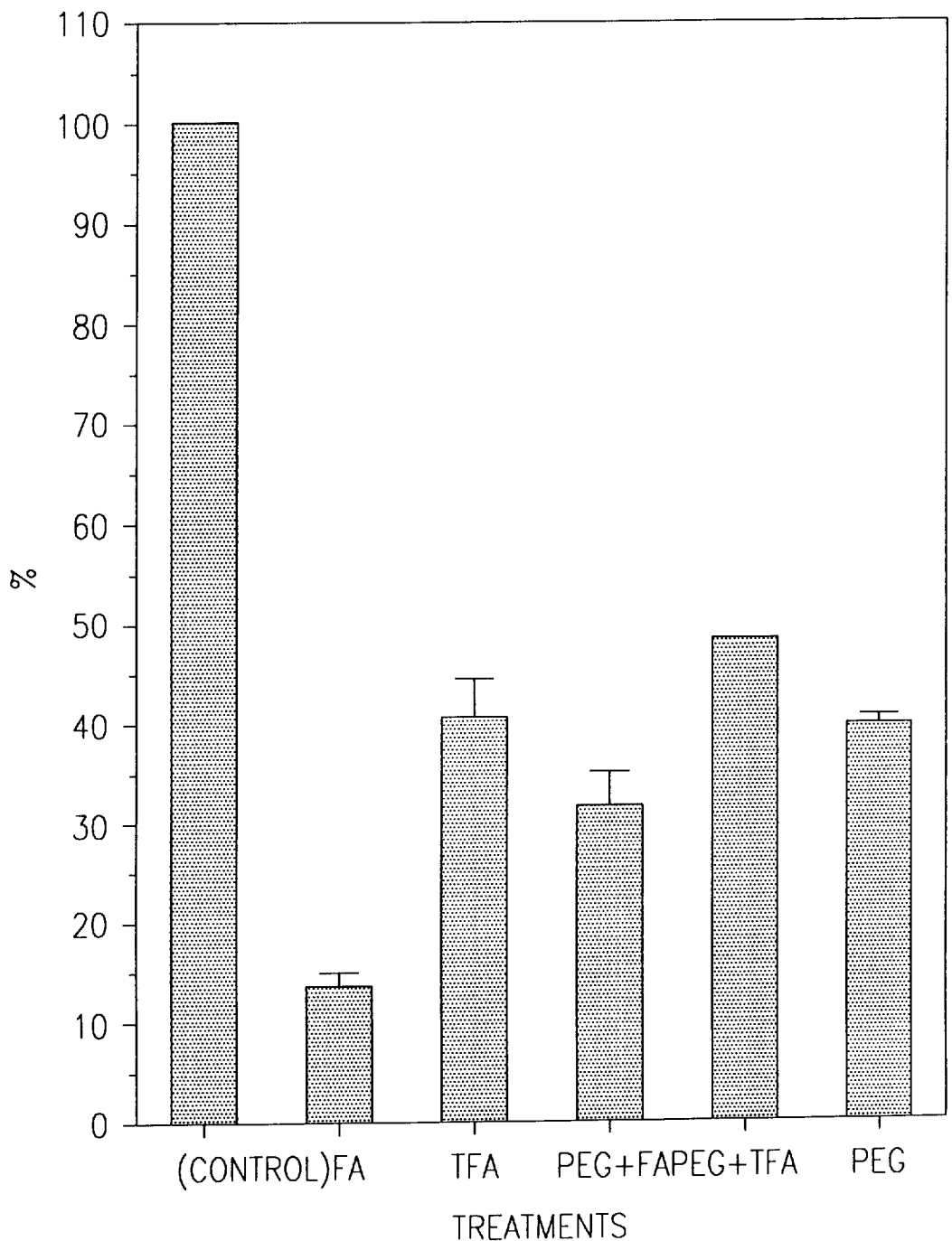
FIG_7

PRION-FREE COLLAGEN AND COLLAGEN-DERIVED PRODUCTS AND IMPLANTS FOR MULTIPLE BIOMEDICAL APPLICATIONS; METHODS OF MAKING THEREOF

CROSS REFERENCE TO RELATED APPLICATIONS

This application claims the benefit of the filing date of U.S. provisional Application No. 60/010,794, filed Jan. 29, 1996, now abandoned, and PCT Application No. PCT/CA97/00070, filed Jan. 29, 1997, now pending.

FIELD OF THE INVENTION

This invention relates to a method of eliminating prion for collagen or collagen-derived products, particularly by dehydrothermal or chemical inactivation.

BACKGROUND OF THE INVENTION

Among biological materials, collagen, particularly type I collagen, is a major component of various connective tissues including bone. The replacement of human tissues with human- or animal-derived tissues such as skin or bone grafts results in the improvement of the wound healing process because of the presence of collagen. Therefore, the application of collagen-derived products as biomaterials has tremendous impact in biomedicine because of (i) the natural structure of these products as a biological support for cells and scaffold for tissue repair or regeneration, (ii) their biodegradability that obviates removal of implants, and (iii) their biocompatibility. Collagen has been used to design biomaterials such as wound dressings, artificial dermis, bone or tendon substitutes, tissue engineered devices, and injectable materials in plastic surgery [1-5]. One of the advantages of using animal collagen, particularly from bovine species, is the facility with which large quantities of pure type I or type I/III collagen can be produced.

The emergence of new viruses and the appearance of new infective diseases require increased vigilance concerning the safety of biologicals, especially since the discovery of transmission of protein such as the prion correlates with infectivity (i.e., bovine spongiform encephalopathy)[6]. The assessment of the safety of a biological product towards prion is complicated by the lack of a test capable of detecting scrapie-like agents in the starting material. Collagen purified from human sources could also be a vector for the human spongiform encephalopathies[7] and, perhaps, viral diseases (known and unknown).

The scrapie agent is extremely resistant to heat and physical inactivation[8]. Prolonged exposure to concentrated NaOH solutions and autoclaving at temperatures above 130° C. can be recommended for routine inactivation and disinfection of scrapie-like agents[9]. However, there is still a debate over whether this procedure simply extends the incubation period[10]. Furthermore, only NaOH can be applied to collagen because autoclave destroys collagen.

Treatment of collagen by NaOH at similar concentrations and incubation periods (as recommended) have been investigated towards the elimination of other infectious agents such as bacterium or viruses (RNA or DNA viruses). In a basic environment, we have shown indirectly by agarose gel that DNA and RNA are not fragmented enough to implement elimination of infectious disease and transmission.

In another study we have compared the effect of glutaraldehyde treatment as usually used to crosslink collagen products (i.e., Yannas' skin; cardiac biological valves; vessel grafts; and other biological implants). Two methods of treating collagen with glutaraldehyde solution have been tested. One is using water and the other diluted acetic acid as buffer to crosslink collagen. The latter condition is described in Yannas' patent U.S. Pat. No. 4,060,081 on his artificial skin. Many investigators claim that glutaraldehyde treatment of collagen and derived products (i.e., gelatin capsules) can sterilize the final crosslinked products. Using the two methods of glutaraldehyde treatment, our investigation (using agarose gel) shows clearly that DNA and RNA incorporated in our collagen are not completely broken down and subsequently the risk of transmission of viruses and bacteria is most probable.

Other treatments such as 8M urea have been also recommended. Nevertheless, partial breakdown of DNA and RNA was observed. This breakdown is partial enough to offer no warranty of virus-free products.

On the other hand, formic acid (FA), SDS, fluorinated alcohols, and trifluoroacetic acid (TFA) have dramatic effects on the prion (PrP27-30) secondary and tertiary structures which correlates with the inactivation of scrapie infectivity[11-12]. There is no suggestion in the art that collagen will resist to those treatments.

As mentioned above, a combination of NaOH and autoclave is currently used to eliminate prion. We have shown that NaOH by itself cannot warrant the breakdown of DNA or RNA. It is further known that autoclaving at about 130° C. destroys collagen. Other procedures making use of severe dehydrothermal treatment are used for crosslinking polymer components. Dehydrothermal treatment also has for effect to sterilize the products as well as crosslinking polymer components. Nobody has investigated as to whether heat sterilization may remove prions while preserving the integrity of collagen-comprising products.

In view of the foregoing, there is a need for a method of making a prion-free collagen-comprising product wherein prion is eliminated while collagen is not substantially denatured beyond a desirable or unavoidable extent.

STATEMENT OF THE INVENTION

It is an object of the present invention to provide a method to eliminate prion from collagen-comprising products while preserving substantially the integrity of those products.

In a particular embodiment of the invention, such a method makes use of a strong acid having a pH solution below about 2. In a preferred embodiment, the strong acid is pure trifluoroacetic acid or fluoroacetic acid (pH 1) applied directly on a lyophilized collagen-comprising product by impregnation. The time of reaction may vary from about 1 to 5 hours depending on the nature of the acid e.g. the more potent is the acid, lesser the time is necessary to eliminate prion without affecting the integrity of the product.

In another embodiment of the invention, dehydrothermal treatment substitutes for the chemical inactivations e.g. the strong acid. In that particular method, collagen a collagen-derivative such as gelatin is submitted to temperature and time conditions which are sufficient to eliminate prion without affecting substantially the integrity of collagen beyond a desirable extent. In a preferred embodiment, those conditions are a temperature of 110° C. and a period of 1 to 3 days, in a dry atmosphere (under high vacuum).

In another embodiment of the invention, the two above-sterilization methods are combined. First, collagen is treated with TFA for a period of time which is dependent on the desirability to convert collagen into gelatin. When a substantive conversion to gelatin is desirable, collagen may be treated with TFA or an acid having an equivalent action, for a period of time which is higher than about 5 hours, preferably between 6 to 12 hours. The collagen or collagen-derivative (e.g., for example, collagen, TFA-treated collagen or gelatin) are then submitted to a dehydrothermal treatment, which has for effect to eliminate prion, if any, and crosslink the product. The heat treatment has for dual effect to stabilize the product by crosslinking and eliminate prion.

It is another object of this invention to-provide products comprising collagen and collagen derivatives prepared by the acid and/or heat-inactivation above processes which have the advantage of achieving a safe prion-free collagen. Collagen as a starting material in the production of collagen products, collagen already/shaped as films, sponges, drug-delivery systems or wound dressings; collagen conjugated to other acid-stable molecules, and collagen derivatives or fragments, are all examples of materials which be subject to inactivation processes.

This invention will be described hereinbelow by way of specific examples and appended figures, which purpose is to illustrate and not to limit the scope of the invention.

BRIEF DESCRIPTION OF THE DRAWINGS

FIGS. 1A–1E. FTIR spectra of collagen materials untreated (A) and treated (for a 1 h exposure period) by formic acid (B); trifluoroacetic acid (C); trifluoroethanol (D), and hexafluoro-2-propanol (E).

FIGS. 3A–3D. FTIR spectra of collagen materials in the amide I region before (a & b) and after (c & d) spectral deconvolution. Untreated collagen (full lines) were compared to collagen treated for 1 h (a & c) or 5 h (b & d) by formic acid (dash-dotted lines); trifluoroacetic acid (dashed lines); trifluoroethanol (dotted lines), and hexafluoro-2-propanol (dashed-double-dotted lines).

FIG. 4. Cell growth. Human dermal fibroblasts were cultivated on multiwell plates in fluid medium contact with collagen sponges which were either untreated (open squares), or treated by exposure to FA (closed triangles), TFA (closed squares), TFE (closed circles), or HFIP (open circles). Cell growth was determined by counting cells as a function of time. Means and standard deviations of the mean are presented (N=18).

FIGS. 5A–5E. Observations of collagen sponges treated with FA (A, B & C); TFA (D), and TFE (E). Prior to implantation (A: Histologic section, x181; B: TEM, x19, 200), the treatment of a porous collagen sponge by FA results in a collapsed structure with collagen bundles (arrows) which have a periodicity (B). Subcutaneous implantations were performed in mice, and sequentially analyzed. Histologic sections of the 30 day retrieved implants are presented (C, D & E: x90). At this period, cell (arrowheads) infiltration is present between the collagen bundles (arrows) of the implanted collagen materials. In B, note the deposition of extracellular matrix (*). In D, fatty tissue (f) was present within the collagen materials as well as inflammatory cells (i).

FIGS. 6A–6C. Average fragment length of nucleic acids contained within bovine type I collagen and added following different chemical treatments of the collagen. Lanes in A contain collagen sponge plus 5 µg of yeast RNA; lanes in B contain collagen sponge plus 5 µg of calf thymus DNA; and lanes in C contain collagen sponge only. These samples were treated with the following chemicals: no chemical (lanes 1), formic acid (lanes 2), trifluoroacetic acid (lanes 3), trifluoroethanol (lanes 4) and hexafluoro-2-propanol (lanes 5). The 1.5% agarose gel was stained with ethidium bromide (1 µg/ml). The first and last lanes of this gel contain HindIII lambda phage+HaeIII digested ϕX174 DNA molecular weight standards, respectively.

FIG. 7. Water uptake of freeze-dried collagen sponges treated by FA or TFA for 1 hr exposure. Composite PEG-collagen materials were also compared before and after treatment with FA or TFA.

DESCRIPTION OF THE INVENTION

Materials and Methods

Chemical Reagents

Figure 2A:
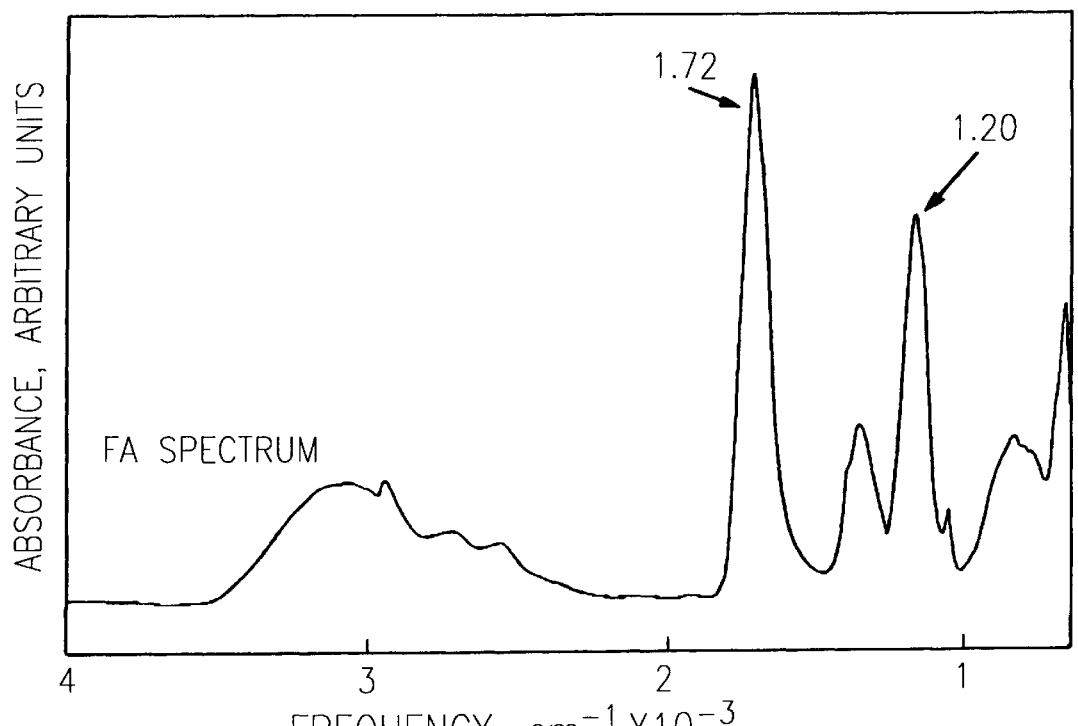
FIG. 2. FTIR spectra of pure formic acid (FA); and trifluoroacetic acid (TFA).

Formic acid (FA) (23.4N) was purchased from BDH Inc. (Ville St-Laurent, QC, Canada); trifluoroacetic acid (TFA) (free acid in ampuls) from Sigma Chemical Co., (St-Louis, Mich., U.S.A.); 2,2,2-Tri-fluoroethanol (99%; TFE), and 1,1,1,3,3,3-Hexafluoro-2-propanol (99%; HFIP) from Aldrich Chemical Company (Milwaukee, Wis., U.S.A.).

Specimen Preparations

Collagen was extracted from adult bovine hide by acetic acid dispersion and purified by NaCl salt precipitation to obtain a dispersion of insoluble collagen fibril bundles[13-14]. The periodicity of these collagen fibrils was mostly preserved as previously reported[14]. Collagen sponges were obtained by freeze-drying a 1% collagen dispersion (w/v collagen to water) as previously described[14]. Sponges were then exposed to pure FA (pH: 1), TPA (pH: 1), TFE (pH: 5), and HPIP (pH: 4.5–5) for different periods, according to the methodology described by Safar et al.[11]. Vacuum dried specimens were then rehydrated in distilled and deionized water with extensive washing for 24 h at room temperature. During this procedure, the pH resumed to a range of the initial water pH at 5–6 in less than 1 h and remained stable. Most samples were then air-dried to be processed for analyses. For the cell culture and animal studies, sponges were manipulated in sterile conditions.

Fourier Transform Infrared Spectroscopy (FTIR)

FTIR spectra were recorded with a Nicolet Magna-550 Fourier transform infrared spectrometer equipped with a MCT/A detector and a germanium coated KBr beamsplitter. One hundred scans were routinely acquired with an optical retardation of 0.5 cm, triangularly apodized and Fourier transform to yield a 2 cm$^{-1}$ resolution. The attenuated total reflectance mode was used to record the infrared spectra of collagen sponges with a Split Pea attachment equipped with a Si hemispherical, 3 mm diameter internal reflection element. Fourier deconvolution of the amide I spectral region was done using a narrowing factor of 7.5 and an apodization filter of 0.14 as described[15]. These parameters were used to minimize side lobes in the 1720–1750 cm$^{-1}$ region where no collagen band was observed. Measurements were made in triplicate on different collagen batches for each treatment, including control.

Differential Scanning Calorimetry (DSC)

The denaturation temperatures were measured on a Perkin Elmer DSC 7 differential scanning calorimeter. To facilitate the measurements, a 3% (v/w) collagen dispersion was produced and then air-dried to obtain a compact film. Specimens were introduced in a clean crimpable aluminum pan and about 15 ml of distilled water was added. A control pan filled with the same volume of distilled water was set in the reference port of the instrument. The DSC was filled with liquid nitrogen and purged with helium. Analyses were performed between −50° C. to 90° C. at the heating rate of 10° C./min. Denaturation temperatures were determined by measuring the temperature reaching the highest point on the denaturation peak. Measurements were made in duplicate and the denaturation temperature values have a ±3° C. accuracy range.

Collagenase Assay

For the collagenase assays, dried collagen sponges were immersed in collagenase (250 units of collagenase per mg of collagen; type IA from Clostridium histolyticum, Sigma) neutral solution (pH 7.5) containing buffer A (25 mM Tris buffer and 10 mM $CaCl_2$). Specimens were incubated at 37° C. and observed at 5 min intervals during the incubation. The incubation period that resulted in complete disappearance (i.e., all fragments) of collagen sponges was considered to be related with the resistance of the materials to enzyme degradation. In addition, hydroxyproline content was measured after a one-hour period of collagenase digestion according to a method previously described[16]. Triplicate samples were assayed and a student's t-test was used for comparison with a level of significance set at ≦0.05.

Fibroblast Cell Cultures

Cell culture investigations were performed with human foreskin fibroblasts, seeded at a low cell density of $1 \times 10^3$ cells/$cm^2$, on the bottom of wells. Collagen materials were introduced in cell culture inserts (3.0 µm polyethylene terephthalate porous filter, from Becton Dickinson Labware). Cells were cultivated in Dulbecco's Modified Eagle Medium (Sigma) supplemented with 5% fetal bovine serum (GIBCO/BRL) and antibiotics, at 37° C. under humid atmosphere in 5% $CO_2$. At 24, 72 h and 7 days, cell counts were determined directly in wells using a supravital DNA stain (Hoechst 33342; Polysciences, Inc.) as described to trace cells[17]. A Wilcoxon rank sum (two tailed) test is was carried out for statistic analysis.

Subcutaneous Implantations

Subcutaneous implantations of sponges were performed in mice under anesthesia. Surgeries were conducted under sterile conditions according to the guidelines of the Canadian Council for Animal Care and after approval by the Institutional Animal Care Committee. Two subcutaneous pockets on each flank were made by a medial incision on the back of each animal. The FA-, TFA-, TFE-, and HFIP-treated sponges (1 cm square) were implanted in the same animal, one sponge in each of the four pockets. Three animals were used for each implantation time period. At 7, 15, 30 and 90 days post-implantation, animals were sacrificed. Collagen specimens were collected and fixed in formaldehyde, processed for histological evaluation (two serial sections) and stained with hematoxylin-phloxin-saffron. Transmission electron microscopy was performed by drying collagen dispersion directly on grids which were then stained with lead citrate and uranyl acetate.

Sample Processing and Agarose Gels for DNA and RNA Assays

For DNA and RNA assays, there were three groups of 5 samples: group 1 included collagen and RNA, group 2 included collagen and DNA, and group 3 included only collagen. For the specimens containing DNA or RNA, calf thymus DNA (Calbiochem Corp.) and yeast RNA (Boehringer Mannheim), were introduced during the dispersion step of collagen sponge production. DNA and RNA were used at a concentration of 0.2–0.5 µg/mg of collagen which corresponded to a final amount of 5 µg of DNA or RNA respectively per sample. For each group, every sample was treated with the chemical agents as described above or non-treated (control group). After chemical treatments, sponges were digested with a highly purified collagenase (type VII from Sigma) at 37° C. in buffer A for 2 h. A proteinase K digestion was performed immediately after the collagenase digestion in a 1.5 ml volume. To the collagenase buffer, NaCl, EDTA pH: 7.8, proteinase K and SDS were added to a final concentration of 85 mM, 12.5 mM, 300 µg/ml and 0.5% respectively. The samples were incubated at 37° C. for 3 h. After 2 h, an additional 200 µg of proteinase K per tube was added if the sponge was not reduced into tiny pieces. Before the three phenol-chloroform extractions, all sponges were totally digested after the 3 h digestion period. To precipitate the nucleic acids, 2 µl of glycogen (20 µg/µl) and 80 µl of NaCl 5 M, 420 µl of $H_2O$ and 4 ml of ethanol 100% were added. The nucleic acids were resuspended in 200 µl of $H_2O$ and transferred into a 1.5 ml microtube. Water was evaporated and 20 µl of $H_2O$ was added to resuspend the nucleic acids in a smaller volume. Five µl of 5× loading buffer [5×TAE (40 mM Tris-acetate and 1 mM EDTA, pH: 8), 0.025% bromophenol blue, 30% Ficoll 400 from Pharmacia in water and 2% SDS] was added. The total volume (25 µl) of each sample was loaded on a neutral agarose gel which was run at 50 volts for 2 h 10 min in TAE.

Results and Discussion

Chemical Treatment of Collagen and its Physicochemical Characteristics

Studies by FTIR spectroscopy and by DSC allow to determine respectively the conformational changes in collagen secondary structures and the temperature required to reach the transition from a triple helix to a random coil structure in collagen molecules. These are related to intra- and inter-molecular bonds.

Figure 2B:
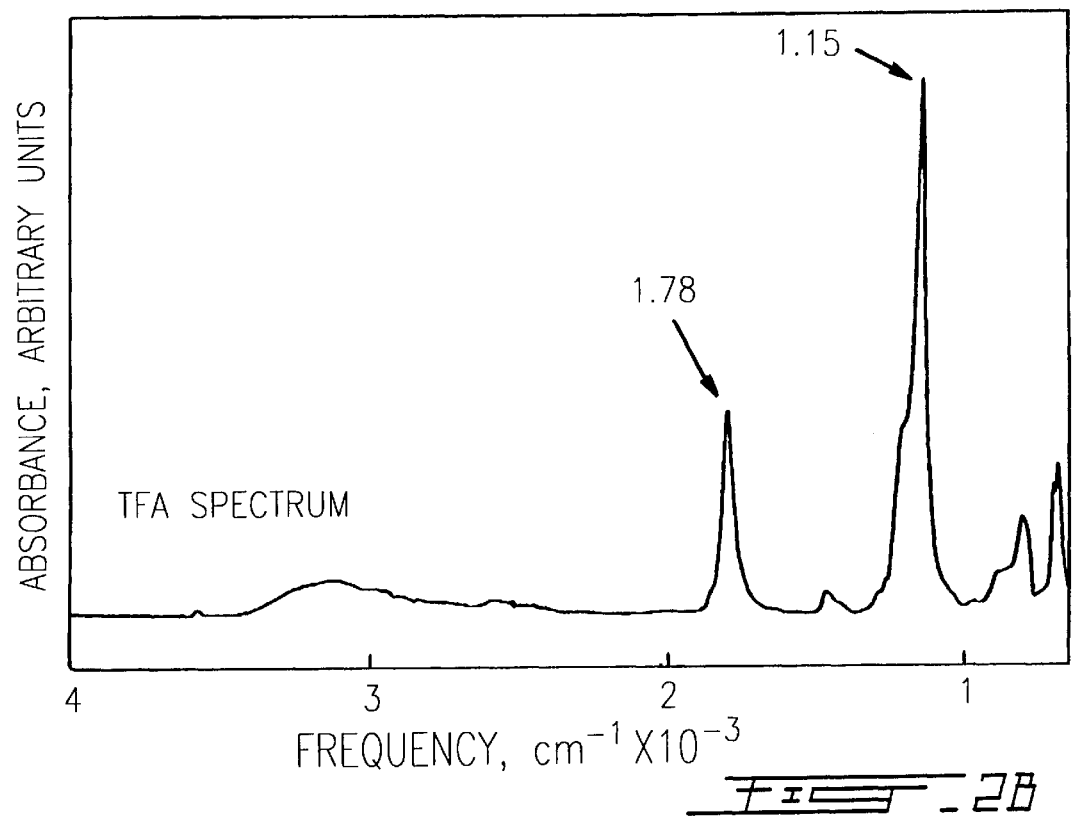

FTIR data indicate that no strong interaction is observed between collagen samples and TFE or HFIP since the infrared spectra of these samples are almost superimposable with that of pure collagen (FIG. 1). Thus, these agents do not promote any chemical modification of collagen and are removed from the collagen sponges during the washing process. On the other hand, the samples treated with FA or TFA show some additional bands, the predominant ones being located at about 1190 and 1715 $cm^{-1}$ for FA and at 1170 and 1782 $cm^{-1}$ for TFA (FIG. 1). The frequencies and the relative intensities of these new infrared peaks closely match those observed in the infrared spectra of pure FA and TFA, showing that these molecules are still present within the collagen structure (FIG. 2). The frequencies of the amide I and amide II bands located near 1650 and 1550 $cm^{-1}$ respectively, due to vibrations of the peptidic bonds of proteins, are indicative of the secondary structure adopted by these molecules. As seen in FIG. 3, the amide I band presents a multicomponent structure due to several factors such as amino acid composition, sequence of residues in triplets, aggregate state of compounds, humidity of samples and type of solvent. The main infrared feature of the amide I band of collagen is centered at 1631 $cm^{-1}$ (FIGS. 3A and 3B) is characteristic of non-imino acid residues in collagen. Although the amide I spectral region remains unchanged for the TFE-treated samples, one can observe a modification of the amide I band shape for the samples treated with FA, TFA and HFIP when compared to untreated collagen. The deconvoluted amide I bands in FIGS. 3C and 3D evidence an additional spectral component at 1655 $cm^{-1}$ which has been previously assigned to imino acid residues in collagen. With the exception of the TFE-treated collagen sponges, all chemical agents lead to a decrease of the 1655/1631 absorbance ratio upon interacting with FA, TFA and HFIP. Such a decrease in the 1655/1631 ratio has been shown to be observed upon collagen denaturation. This modification seems to occur at the first stage of the treatment since the amide I region of the infrared spectra of samples treated for 1 hr are already modified with respect to that of untreated collagen. In addition, the relative intensity of the 1655 and 1631 cm$^{-1}$ features for samples treated for 1 h are very similar to that of samples treated for a 5 h period. However, the infrared spectrum of TFA-treated sample after a 5 h exposure period shows a considerable increase of the band width of the amide I feature due to the presence of spectral contribution of TFA at 1740 cm$^{-1}$. Thus, the amount of TFA present in collagen is higher after an exposure for 5 h than that of 1 h. The changes in structure conformation could probably enhance trapping and grafting of FA or TFA as exposure time increases. A denaturation of collagen into gelatin may be exhibited by an enlargement of the deconvoluted amide I feature. However, the spectra of pure gelatin (i.e. heating collagen) was found even larger than that after TFA (data not shown). On the other hand, the formation of FA salt with the basic groups of proteins has been described and direct binding of FA at peptide bounds is also a possibility. These phenomena suggest that FA may binds to our collagen. It has been previously shown that TFA-casted polymer of poly-glycine results in almost fully extended peptide chains, forming β-like structure configuration in either parallel or antiparallel sheets. Similar events occur when poly-L-lysine is dissolved in TFA, with reversibility. These events could occur in TFA-treated collagen. Furthermore, perturbation of hydrogen bonds as observed with organic solvents induces disturbances in the hydration of collagen shell which could affect the self-association of collagen fibrils by hydrophobic effects. The latter may account for the destabilization of the collagen structure.

The thermotropic transition associated with the denaturation of untreated collagen leads to the obtention of a large endotherm spanning from 45 to 80° C. centered at 61+3° C. (Table 1). This denaturation temperature is in agreement with the value of 65° C. reported for collagen extracted from bovine pericardia[22]. All chemically treated collagen sponges, with the exception of the one with TFE which induced no significant modification, showed a significant decrease of the denaturation temperature (Table 1). TFA induced the most important decrease of the denaturation temperature, particularly after a long period of exposure to chemical agents. The decrease of the denaturation temperature observed for FA-, TFA- and HFIP-treated collagen is probably related to the secondary structure modification. These agents may also lead to a decrease of hydrogen bonds within the collagen structure. On the other hand, the endotherm temperature after the 5 h exposure to TFA is close to that observed with gelatin (data not shown).

Chemical Treatment of Collagen and its Biological Properties

During collagenase digestion, complete degradation of untreated collagen sponges occurred within the same period (from 57 to 73 minutes averages) as treated collagen, except that HFIP-treated collagen was significantly more rapidly degraded than was collagen treated with FA or TFE. However, the amounts of released hydroxyproline after 1 h of collagenase were found statistically close to each other. Since collagenase targets the aminoacid sequence within the triple helix portion of collagen, this structure may be partially preserved after chemical treatments.

In cell culture, the determination of cell growth can reflect the possibility of leakage of chemical agents or by-products from materials. Cell growth on treated collagen was increased as a function of time (FIG. 4), close to that seen with control sponge, except with TFE-treated sponges. In the latter conditions, cell growth was significantly inhibited at day 7. An explanation for this inhibition cannot be clearly established or related to specific modifications. Conversely, it appears that eventual leakage of residual FA or TFA products or by-products, as shown by FTIR, has not targeted cells in culture.

Untreated collagen materials prior to implantation appeared as periodic collagen fibril bundles forming a porous structure[14-23]. Similar structures were observed in TFE- or HFIP-treated collagen. In opposite, collagen fibril bundles were closely packed (FIG. 5A), resembling a collapsed pore structure in FA- or TFA-treated samples. These fibrils remained periodic following FA treatment (FIG. 5B), but not with TFA, as observed by transmission electron microscopy. The latter observation (i.e., TFA treatment) suggests that denaturation occurred in each fibril without entirely melting the whole collagen material. Conversely, denaturation by FA treatment may be limited to some collagen fibrils.

Studies of in vivo behaviour of these materials allows to investigate their biological properties within a complex cell and tissue environment. After implantation for 7 days, cell infiltration consisted of few inflammatory cells and fibroblasts within the collagen implants. Inflammatory reaction was also present in the tissue surrounding the implant, particularly in sponges treated by TFA and HFIP (Table 2). By 15 days, infiltration by inflammatory cells and fibroblasts was present within the implants treated particularly with FA, TFE and HFIP. Adipocytes or fatty degenerescence was observed within collagen materials treated by TFE. Inflammation was especially noticeable in the periphery of TFA-treated collagen. By 1 month, cell infiltration occurred in all chemically-treated sponges (FIG. 5). With FA-, HFIP-, and TFE-treated collagen, cell infiltration was present within the whole interior of collagen materials and in addition, new connective tissue appeared at various sites between the implanted collagen bundles. With TFA-treated collagen samples, the implant appeared partially resorbed with fatty tissue accumulation and persistence of an inflammatory reaction. By 90 days, implants had been largely resorbed, although some residual collagen was observed, except with HFIP-treated collagen for which no implant was retrieved. After FA and TFA treatments which exhibit significant decrease in denaturation temperature, the residual collagen was surrounded by a slight inflammatory reaction and infiltrated by newly deposited collagen. The inflammatory reaction was minimal in the periphery and the interior of FA-treated implants compared to other treatments. In addition, the response lasted apparently for less than 30 days. These responses were also observed with sponges treated by TFE. In opposite, TFA-treated sponges induced an important inflammatory response that could be explained by the presence of a high residue of TFA within collagen compared to those treated by FA. Inflammatory reaction to HFIP-treated sponges was apparently important, but limited to the early period of implantation.

In comparison to previous studies[23-24] using collagen sponges as a wound scaffold, the implantation of a collapsed porous structure resulting of FA and TFA treatments induces a rapid cell infiltration. Similar phenomena have been described with denaturated collagen implants or after blending collagen fibrils with gelatin[25,26]. Denaturated and nondenaturated collagen may be present in our material as shown by FTIR and DSC. Collagen in acids swells with alteration of fibril lengths and thicknesses, while the triple chain units remain intact[27]. With FA or TFA treatment, it is less probable that under acid treatment collagen converts totally to gelatin since our starting collagen consists of rigid fiber units that can slow the denaturation process through the resistance force of these fibers. However, the treatment by TFA, more specifically after a 5 h exposure, probably induces more dissociation of collagen fibrils than with FA, as demonstrated with denaturating agents and by our transmission electron microscopic observation. Since increasing potential of denaturation occurred after long exposure to chemical agents, the 1 h exposed specimens have been investigated towards cell culture and in vivo biocompatibility.

Effects of Chemical Treatments on Nucleic Acids in Collagen

Analysis of single-strand RNA fragment and double-stranded DNA fragment mobility distribution on agarose gels is a useful method for determining the frequency of strand breaks which is correlated with the degree of nucleic acid degradation (reviewed in Drouin et al.,[29]). Neutral agarose gel can visualizes as little as 2 ng in a 0.5-cm-wide band[30]. The sensitivity is 5- to 10-fold lower for single-stranded DNA and RNA than for double-stranded DNA. This means that about 20 ng of single-stranded nucleic acids are needed to be easily detected. The collagen obtained from bovine hide does contain some nucleic acids (FIG. 7, lanes in C). These nucleic acids are likely to be mainly RNA with an average fragment length inferior to 100 nucleotides. The upper part of the smear is probably aggregated ribosomal RNA and tRNA. DNA likely represents a small part of the nucleic acids present in the bovine hide extracts. The presence of minidose of nucleic acids could be due to (i) bacteria as demonstrated by microbiological analysis (environmental bacillus and mycobacterium: "data not shown"); (ii) viruses (non-demonstrated), and/or (iii) residues of cells remaining after hair removal from bovine skin at the tannery, and/or after purification by acetic acid dispersion and salt precipitation. No cell nucleus was found to be present in observations of histological sections of freeze-dried purified collagen and virgin collagen sponges using specific DNA dye ("data not shown").

On the other hand, TFA hydrolyzed any nucleic acids to very small fragments (less than 10 nucleotides); even the added DNA and RNA were totally degraded (lanes A3 and B3, FIG. 6). FA also hydrolyzed any nucleic acids contained in the collagen sponges to very small fragments which were not recovered, whereas the added RNA and DNA were degraded to an average fragment length of less than 40 nucleotides. The other chemical treatments did not seem to induce any significant amount of strand breaks (lanes A4, B4 and C4, FIG. 6). In all likelihood, the very acidic conditions of the FA (pH: 1) and TFA (pH: 1) treatments caused extensive DNA denaturation, depurination of the nucleic acids, and hydrolysis of the phosphodiester bonds of both RNA and DNA. Conversely, treatment of collagen by 1N NaOH, as recommended by most companies producing collagen, does not break down DNA or RNA as recently demonstrated by neutral gel agarose (data not shown).

Every chemical treatment tested in this work involves either a strong (pH: 1) or a mild (pH: 4.5–5) acidic environment, and treatments were performed at room temperature for at least 1 h. Under the strong acidic conditions, there are denaturation of the DNA, an extensive depurination of both DNA and RNA, and hydrolysis of the phosphodiester bonds of both polydeoxyribonucleotides and polyribonucleotides[31]. The purine residues are readily removed from DNA by mild acid treatment. In mild acidic conditions, DNA is partially denaturated and partially depurinated; RNA is basically untouched and very few phosphodiester bonds are hydrolyzed in both RNA and DNA. In summary, strong acid treatment of collagen sponges definitively leaves DNA, too depurinated, and RNA and DNA with too many strand breaks to be usable by any DNA or RNA polymerases to be infectious; whereas mild acidic treatment leaves RNA molecules which can be easily copied to synthesize DNA while the degree of depurination of the DNA might be so important that its infectivity will be precluded. Furthermore, treatment by a chemical scrapie inactivator (e.g., FA or TFA) induced the loss of the β sheet-like secondary and tertiary structure of prion that correlates with inactivation of scrapie infectivity[11]. Based on the results of the present study concerning the degradation of nucleic acids by FA and TFA treatments and those previously reported[11], we can conclude that the chemically-treated collagen lacks both scrapie infectivity and viral transmission. In conclusion, such a chemical treatment could constitute a method to produce safe collagen/gelatin materials protected against prions and viruses. FA seems to be the most efficient of the four tested agents because of its activity as a chemical inactivator in degrading nucleic acids, and its use results in a good biocompatible collagen/gelatin material, despite its presence within the collagen molecule. The latter induces only a temporary inflammatory response, with minimal inflammation as observed with other biodegradable and non-biodegradable biomaterials.

From the above results, it can be deduced that the two acids which achieved elimination of prion are strong organic acids having a pH of about 1. The two other compounds having a pH of about 5.0 were not efficient. Other strong organic and/or inorganic acids may be equivalent to TFA and FA provided that THEY achieve a solution pH below about 2.0; and provided that they do not degrade collagen to an undesirable extent. The time of reaction may be adjusted in function of the acidic strength of the acid agent.

Dehydrothermal Treatment:

As mentioned above, a plurality of known sterilizing procedures have been tried for the production of safe collagen products (e.g. NaOH, glutaraldehyde, urea). From the recommended use of NaOH as a treatment of collagen, one can deduce that a heat treatment is to be avoided. We however tried to sterilize collagen, using milder conditions than autoclaving at 134° C. Collagen was dehydrated under vacuum for 1–3 days at 110° C. in an oven. Collagen was slightly crosslinked and sterile upon treatment, without denaturation. In these conditions, we have analyzed, by agarose gel, DNA and RNA degradation, and observed a complete break down of these molecules (using DNA and RNA added to collagen). The time of dehydrothermal treatment may vary for 1 to 3 days when the temperature is fixed to 110° C., can be more or less shortened at higher temperatures or lengthened at lower temperatures.

Since autoclaving is not desirable for maintaining collagen integrity, it is therefore apparent that there is a limit temperature and pressure value beyond which collagen is destroyed in an unacceptable proportion, and this is observed either in wet conditions as occurred in autoclave or in dry heating under atmospheric humidity. If any water vapour or humidity is not completely removed (for example using a high vacuum) prior to increasing temperature, collagen will begin to denature and then be destroyed sooner than viruses, bacteria or prions.

Thermal treatment may be applied directly to gelatin, and will have as a double advantage to stabilize gelatin by crosslinking and to produce a safe prion-free product. If gelatin is prepared by treating collagen with a strong acid like TFA for a prolonged time (more than about 5 days), heat treatment would provide a double safe product (TFA and heat are two process steps eliminating prion) and will also stabilize gelatin (which is an altered collagen). Crosslinked gelatin could be used to implement enteral resistance of a gelatin capsule for drug delivery, for example.

Properties of Collagen Sponges Treated With TFA as Drug Delivery Systems:

(i) The treatment of collagen with TFA (1 hr exposure) induced high water adsorption and absorption (see FIG. 7) while FA treatment appeared to impair water sorption. This has been also observed with the absorption of peptides such as growth factors. Our investigation showed that radiolabeled growth factor is uniformly distributed within the collagen porous structure treated with TFA while after FA treatment the distribution of radiolabeled growth factor remained around the sponge as determined by autoradiography. TFA property is very interesting to achieve the design of drug absorption onto collagen materials such as that currently described.

(ii) A stable porous structure of collagen sponge, free of prions and viruses can be used as a wound dressing or drug delivery system. Collagen materials which have been stabilized by polyethylene glycol (PEG) as described in the patent publication CA 2,164,262 (PEG-collagen) can be treated by FA or TFA. However, the treatment with FA or TFA should be performed after PEG grafting in order to preserve the porous structure. These composite products have been investigated towards their biocompatibility. They offer similar behaviour than that described for untreated PEG-collagen. Results in cell culture show no cytotoxicity of the products (cell growth was similar to that of the control), and animal studies (mice) have shown slight inflammatory reaction with cell infiltration. The porous structure remained stable for 180 days in mice, except for PEG-collagen treated by TFA. The latter lasted for 90 days of implantation, biodegradation occurred then. This variety of stability can be beneficial to offer various products with a range of biodegradation rates. A PEG-collagen treated with TFA could be further submitted to severe dehydrothermal treatment, which promotes crosslinking and increases stability. We have verified whether PEG-grafted to collagen impairs DNA and RNA destruction by FA or TFA treatment. Gel agarose showed clearly the breakdown of nucleic acids as reported previously on collagen sponges.

(iii) When FA and TFA are introduced before the PEG treatment, collagen sponges failed to remain porous. However, resulting collagen products allowed cell infiltration, with some delay during the wound healing process. This interesting property can be used to stabilize capsules made of gelatin (such as induced by TFA) as mentioned above.

Figure 8:
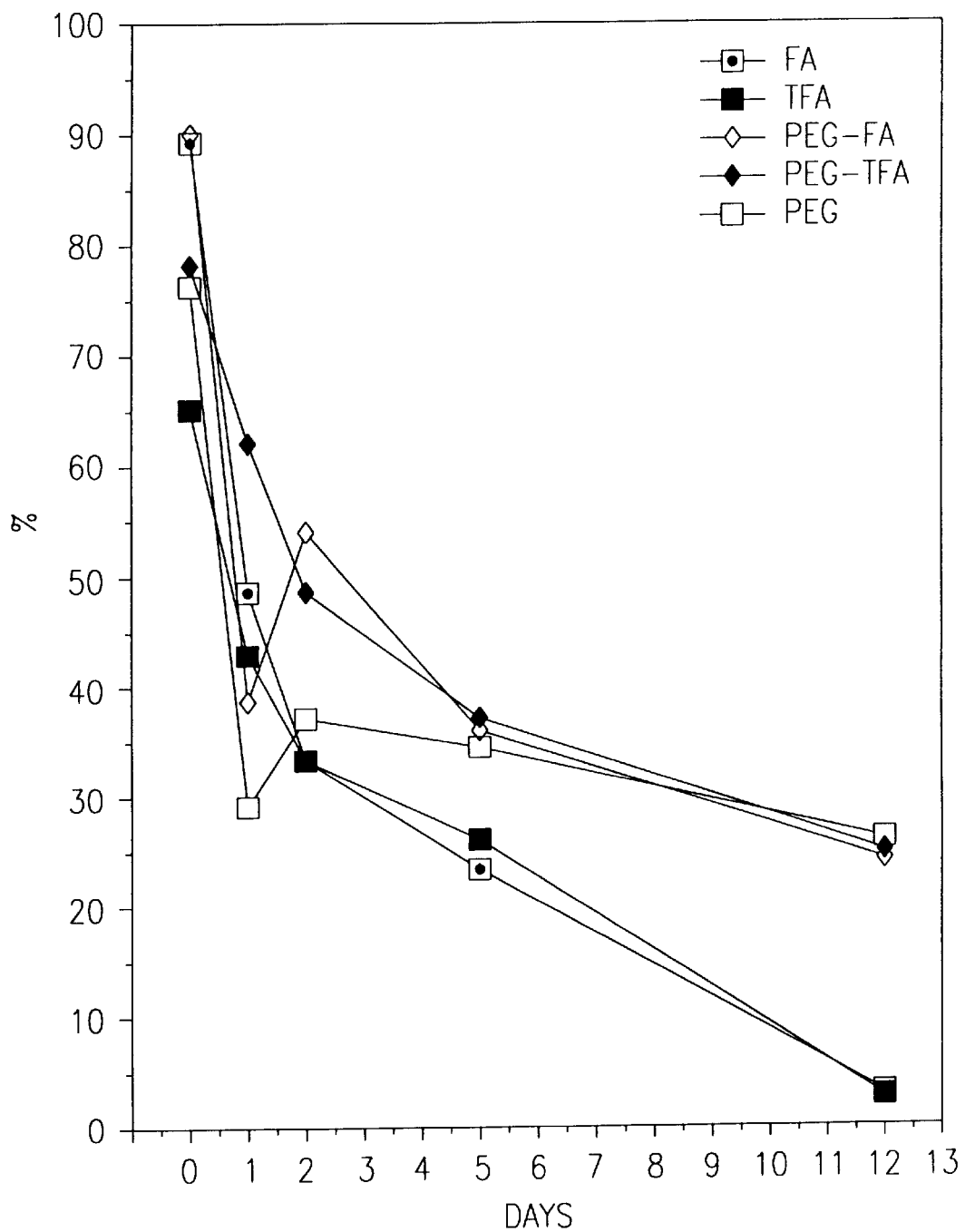
FIG. 8. Kinetic curves of radiolabeled growth factor ($^{125}$I-bFGF) absorbed in collagen and PEG-collagen sponges treated by FA or TFA for 1 hr. Sponges were implanted for different periods and radioactivity was measured as a function of time post-implantation.

(iv) The composite PEG-collagen can be useful as a growth factor delivery system, because it can maintain higher concentrations of growth factor, compared to collagen alone. The treatment of this composite PEG-collagen by FA or TFA preserved in vivo this property (see FIG. 8). In addition, by autoradiography, the growth factor is well distributed within the porous structure.

Transparent Products and Implants

Transparent or clear collagen is obtained by prolonged exposure to TFA which can vary from 6 to 12 hours, depending on the collagen batch. Thus, treated collagen sponges behave as hydrogel-like materials with a transparency property. Treated collagen film (air-dried dispersion) is more fragile than treated collagen sponges (or hydrogels).

Transparent collagen materials can be produced in various thicknesses ranging from 10 to 500 $\mu$m. The concentration of collagen dispersion is also an important parameter in getting transparency. Thus, a 0.5 to 0.75% (weight of collagen to volume of water) appeared transparent. At 1% collagen dispersion, transparency was never reached.

Figure 9:
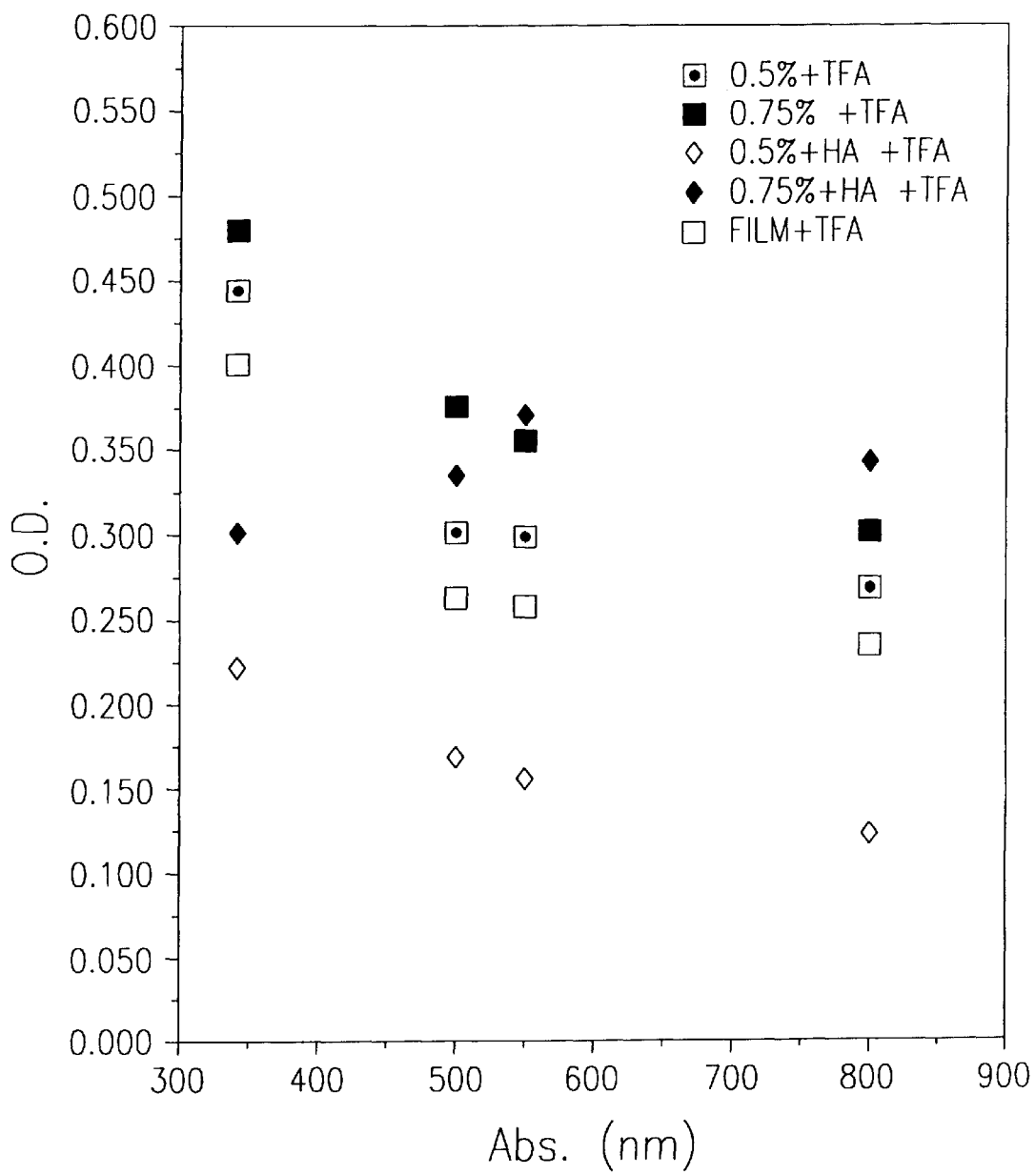
FIG. 9. Optic densities of transparent collagen hydrogels and films. Various wavelengths were investigated towards a variety of collagen materials treated by TFA for 8 hrs.

On the other hand, the addition of hyaluronic acid (HA), a glycosaminoglycan, enhances the transparency of the collagen (5% (w/w) HA per weight collagen, HA being added to the collagen dispersion). This has been determined by measuring optic density at different wavelength adsorption (see FIG. 9). The addition of other glycosaminoglycans and proteoglycans and other percentages of HA can be also beneficial in getting a more transparent material. Furthermore, the addition of hyaluronic acid stimulates cell infiltration into the implant as demonstrated in cell culture.

Those transparent or clear materials can be used for ocular applications, and more particularly for transparent corneal wound dressings. Collagen shields are used for the same purpose, however, they are produced from bovine, swine, or human, but their safety remained an issue. Our product could safely be used.

This invention has been described hereinabove and it will become readily apparent to the skilled reader that modifications can be made thereto without departing from the above teachings. These modifications are under the scope of the invention as defined in the appended claims.

REFERENCES

1. E. Bell, B. Ivarsson, and C. Merril, "Production of a tissue-like structure by contraction of collagen lattices by human fibroblasts of different proliferative potential in vitro," *Proc. Natl. Aca Sci. USA,* 76, 1274–1278 (1979).
2. I. V. Yannas, J. F. Burke, D. P. Orgill, and E. M. Skrabut, "Wound tissue can utilize a polymeric template to synthesize a functional extension of skin," *Science,* 215, 174–176 (1982).
3. T. Miyata, T. Taira, and Y. Noishiki, "Collagen engineering for biomaterial use," *Clin. Mater.* 9, 139–148 (1994).
4. G. Ellender, R. Papli, R. Hammond, K. Mitrangas, J. F. Bateman, V. Glattauer, J. M. Thyer, J. A. Werkmeister, and J. A. M. Ramshaw, "Osteogenic capacity of collagen in repair of established periodontal defects," *Clin. Mater.* 9, 201–209 (1994).
5. J. Keefe, L. Wauk, S. Chu, and F. DeLustro, "Clinical use of injectable bovine collagen: A decade of experience," *Clin. Mater.,* 9, 155–162 (1994).
6. S. B. Prusiner, "Novel proteinaceous infectious particles cause scrapie," *Science,* 216, 136–144 (1982).
7. S. B. Prusiner, "Inherited prion diseases," *Proc. Natl. A cad. Sci. USA,* 91, 4611–4614 (1994).
8. P. Brown, P. P. Liberski, A. Wolff, and D. C. Gajdusek, "Resistance of scrapie infectivity to steam autoclaving after formaldehyde fixation and limited survival after ashing at 360 degrees C: Practical and theoretical implications," *J.Infect. Dis.,* 161, 467–472 (1990).
9. R. N. Rosenberg, C. L. White, P. Brown, D. C. Gajdusek, J. J. Volpe, J. Posner, and P. J. Dyck, "Precautions in handling tissues, fluids and other contaminated material from patients with documented or suspected Creutzfeldt-Jakob disease," *Ann. Neurol.,* 19, 75–77 (1986)
10. J. Tateichi, T. Tashima, and T. Kitamoto, "Inactivation of Creutzefelt-Jakob disease agent," Ann. Neurol., 24, 466- (1988).

11. J. Safar, P. P. Roller, D. C. Gaidusek, and C. J. Gibbs, "Thermal stability and conformational transitions of scrapie amyloid (prior) protein correlate with the infectivity," Protein Sci., 2, 2206–2216 (1993).
12. W. E. Klunk, C.-J. Xu, and J. W. Pettegrew, "NMR identification of the formic acid modified residue in Alzheimer's amyloid protein." J. Neurochem., 62, 349–354 (1994).
13. E. J. Miller, and R. K. Rhodes, "Preparation and characterization of the different types of collagen," Methods Enzymol., 82, 33–64 (1982).
14. M.-F. Côté, E. Sirois, and C. J. Doillon, "In vitro contraction rate of collagen in sponge shape matrices," J. Biomater. Sci. -Polym. Ed., 3, 301–313 (1992).
15. P. R. Griffiths, and G. L. Pariente, "Introduction to spectral deconvolution," Trends Anal. Chem., 5, 209–215 (1986).
16. R. A. Berg, "Determination of 3- and 4-hydroxyproline," Methods Enzymol., 82, 372–398 (1992).
17. J. L. Ellwart, and P. Dorner, "Vitality measurement using spectrum shift in Hoechst 33342 stained cells." Cytometry, 11, 239–243 (1990).
18. Y. A. Lazarev, B. A. Grishkovskii, and T. B. Khromova, "Amide I band of IR spectrum and structure of collagen and related polypeptides." Biopolymers, 27, 1449–1678 (1985).
19. K. Payne, A. Veis, "Fourier transform IR spectroscopy of collagen and gelatin solutions: deconvolution of the amide I band for conformational studies." Biopolymers, 27, 1749–1760 (1988).
20. A. Veis, The Macromolecular Chemistry of Gelatin, Molecular Biology, volume 5, Horecker, B. Kaplan, N. O. & Scheraga H. A. (eds.), Academic Press, New York-London, (1964).
21. A. V. Kajava, "Molecular packing in type I collagen fibrils. A model with neighbouring collagen molecules aligned in axial register." J. Mol. Biol., 218, 815–823 (1991).
22. J. M. Lee, C. A. Pereira, D. Abdulla, W. A. Naimark, and I. Crawford, "A multi-sample denaturation temperature tester for collagenous biomaterials," Med. Eng Phys., 17, 115–121 (1995).
23. C. DeBlois, M.-F. Côté, and C. J. Doillon, "Heparin-FGF-fibrin complex: In vitro and in vivo applications to collagen-based materials," Biomaterials, 15, 665–672 (1994).
24. C. J. Doillon, M. G. Dunn, R. A. Berg, and F. H. Silver, "Collagen deposition during wound repair," Scan. Microsc., 2, 897–903 (1985).
25. K. Yoshizato, and E. Yoshikawa, "Development of bilayered gelatin substrate for bioskin: a new structural framework of the skin composed of porous dermal matrix and thin basement membrane," Mater. Sci. Eng. C-Biomimetic Materials, Sensors & Systems, 1, 95–105, (1994).
26. M. Koide, K. Osaki, J. Konishi, K. Oyamada, T. Katakura, A. Takahashi, and K. Yoshizato, "A new type of biomaterial for artificial skin: dehydrothermally cross-linked composites of fibrillar and denaturated collagens," J. Biome. Mater. Res., 27, 79–87 (1993).
27. GN Ramachandran, in Collagen, Ramanathan N. (ed.), Wiley Interscience, New York, (1962).
28. J. H. Lillie, D. K. MacCallum, L. J. Scaletta, and J. C. Occhino, "Collagen structure: Evidence for a helical organization of the collagen fibril," J. Ultrastruct. Res., 58, 134–143 (1977).
29. R. Drouin, S. Gao, G. P. Holmquist, "Agarose gel electrophoresis for DNA damage analysis". In: Technologies for detection of DNA damage and mutations. G. P. Pfeifer (ed), Plenum Press, New York, 1996, (in press).
30. J. Sambrook, E. F. Fritsch, and T. Maniatis, eds. Molecular Cloning: A Laboratory Manual 2nd Ed. Cold Spring Harbor Laboratory Press, Cold Spring Harbor, N.Y., 1989.
31. D. M. Brown, "Chemical reactions of polynucleosides and nucleic acids" in Basics Principles in Nucleic Acid Chemistry Vol II, Ts'O Paul OP ed. Academic Press, New York-London, pp.1–90 (1974).

TABLE 1

Denaturation temperature for the untreated and chemically treated collagen sponges

| Collagen | A | B |
|---|---|---|
| | Denaturation temperature (± 3° C.) | |
| untreated | 61 | 61 |
| FA | 41 | 36 |
| TFA | 35 | 29 |
| TFE | 57 | 58 |
| HFIP | 43 | 39 |

Collagen sponges where chemically treated with FA, TFA, TFE or HFIP for 1 h (A) and 5 h (B) exposure periods.

TABLE 2

Qualitative scale of the inflammatory reactions after implantation of chemically-treated collagen sponges

| Days | Formic acid | | Trifluoroacetic acid | | Trifluoro ethanol | | Hexafluoro-2-propanol | |
|---|---|---|---|---|---|---|---|---|
| | P | I | P | I | P | I | P | I |
| 7 | ± | ± | ++ | ± | ± | ± | ++ | + |
| 15 | ± | ± | ++ | + | + | + | ± | + |
| 30 | + | 0 | + | + | ± | 0 | ± | ± |
| 90 | ± | 0 | ± | 0 | 0 | 0 | Not retrieved | |

The inflammatory reaction was qualitatively appreciated following a relative scale: ++ for extensive; + for moderate; ± for light; and 0 for nil to sparsely light. Reactions were noted in the periphery (P) and inside (I) of the implants.

We claim:

1. A process for producing a compound comprising collagen free of prion, comprising:
   a) treating said compound with an organic acid having a solution pH equal to or below 2 for a period of time of at least one hour, wherein said prion is eliminated while said compound comprising collagen is not denatured after said treatment process, while at least a part of said collagen is converted into gelatin.

2. A process as defined in claim 1, wherein said acid is a pure undiluted organic acid.

3. A process according to claim 1, wherein said period of time is about one hour.

4. A process according to claim 1, wherein said compound comprising collagen is obtained from a solution comprising about 0.5 to about 0.75% (w/v) collagen, and wherein said compound comprising collagen obtained at the end of the organic acid treatment step is transparent.

5. A process according to claim 1, wherein said compound comprising collagen is a polyethylene glycol-grafted collagen which is formed as a porous material.

6. The process of claim 1, further wherein and infectious agents are eliminated.

7. A process according to claim 1, wherein said organic acid is trifluoroacetic acid or formic acid.

8. A process according to claim 7, wherein said organic acid is pure formic acid.

9. A process according to claim 7, wherein said organic acid is pure trifluoroacetic acid.

10. A process as defined in claim 1, wherein said period of time is at least five hours, whereby the prion is eliminated while at least a part of collagen is converted into gelatin.

11. A process according to claim 10, which further comprises the step of crosslinking the gelatin after the organic acid treatment step.

12. A process according to claim 11, wherein the crosslinking is achieved by an organic aldehyde or dehydrothermal treatment.

13. A process according to claim 12, wherein the dehydrothermal treatment comprises heating at about 110° C. for about 1 to 3 days under high vacuum.

14. A process for producing a compound comprising collagen which is free of prion which comprises treating the compound comprising collagen to a temperature of about 110° C. for a period of time and conditions sufficient to eliminate prion while said compound comprising collagen is not denatured after said treatment process, while at least a part of said collagen is converted into gelatin.

15. A process according to claim 14, wherein said period of time is comprised between about 1 day to about 3 days under high vacuum.

* * * * *

UNITED STATES PATENT AND TRADEMARK OFFICE
CERTIFICATE OF CORRECTION

PATENT NO.    : 6,197,935 B1
DATED         : March 6, 2001
INVENTOR(S)   : Doillon et al.

It is certified that error appears in the above-identified patent and that said Letters Patent is hereby corrected as shown below:

<u>Column 14,</u>
Line 66, at claim 6, after "wherein", please delete "and".

Signed and Sealed this

Twenty-fifth Day of September, 2001

*Attest:*

NICHOLAS P. GODICI
*Attesting Officer*   *Acting Director of the United States Patent and Trademark Office*